United States Patent
Yamaguchi

(10) Patent No.: US 9,638,629 B2
(45) Date of Patent: May 2, 2017

(54) MASS ANALYSIS DATA ANALYZING METHOD AND APPARATUS

(75) Inventor: Shinichi Yamaguchi, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 507 days.

(21) Appl. No.: 14/236,497

(22) PCT Filed: Aug. 3, 2011

(86) PCT No.: PCT/JP2011/067784
§ 371 (c)(1),
(2), (4) Date: Jan. 31, 2014

(87) PCT Pub. No.: WO2013/018211
PCT Pub. Date: Feb. 7, 2013

(65) Prior Publication Data
US 2014/0163902 A1    Jun. 12, 2014

(51) Int. Cl.
*G01N 31/00* (2006.01)
*G01N 21/31* (2006.01)
(Continued)

(52) U.S. Cl.
CPC ........... *G01N 21/31* (2013.01); *G06F 19/703* (2013.01); *H01J 49/0036* (2013.01); *H01J 49/0045* (2013.01)

(58) Field of Classification Search
CPC ............ H01J 49/0036; G01N 33/6848; G01N 33/6851
See application file for complete search history.

(56) References Cited

U.S. PATENT DOCUMENTS 7,932,486 B2 * 4/2011 Sano ................. G01N 33/6848
250/281
2006/0085142 A1 4/2006 Mistrik
(Continued)

FOREIGN PATENT DOCUMENTS

EP  2 208 990  7/2010
EP  2 208 991  7/2010

OTHER PUBLICATIONS

Chinese Office Action issued May 13, 2015 in Chinese Patent Application No. 201180072499.1.
(Continued)

*Primary Examiner* — Elias Desta
(74) *Attorney, Agent, or Firm* — Sughrue Mion, PLLC

(57) ABSTRACT

A method and apparatus for estimating the structure of an unidentified substance produced from an original substance having a known structural formula through partial structural change caused by metabolism or the like. A mass difference between a product ion, originating from the unidentified substance and having a partial structure including a structural change site, and a product ion, originating from the original substance and having a partial structure prior to the structural change, is equal to the mass difference between the original substance and the unidentified substance. Therefore, when pairs of product ions each having such a mass difference are selected to be compared with partial structures obtained from the known structural formula of the original substance, a minimum common partial structure having the structural change site is obtained.

6 Claims, 7 Drawing Sheets

(51) Int. Cl.
*H01J 49/00* (2006.01)
*G06F 19/00* (2011.01)

(56) References Cited

U.S. PATENT DOCUMENTS

2008/0067344 A1 3/2008 Yamaguchi et al.
2010/0288917 A1* 11/2010 Satulovsky ......... H01J 49/0031
250/282

OTHER PUBLICATIONS

European Search Report issued Feb. 6, 2015 in European Patent Application No. 11870202.6.

* cited by examiner

STRUCTURAL FORMULA OF ORIGINAL SUBSTANCE

MS² SPECTRUM OF ORIGINAL SUBSTANCE

Fig. 6

PRODUCT IONS ORIGINATING FROM ORIGINAL SUBSTANCE → MASS DIFFERENCE = 0

PRODUCT IONS ORIGINATING FROM METABOLITE ↓

MASS DIFFERENCE = 16

MASS ANALYSIS DATA ANALYZING METHOD AND APPARATUS

CROSS REFERENCE TO RELATED APPLICATIONS

This application is a National Stage of International Application No. PCT/JP2011/067784, filed on Aug. 3, 2011, the contents of all of which are incorporated herein by reference in their entirety.

TECHNICAL FIELD

The present invention relates to a method and an apparatus for analyzing the structure of a substance through analysis of data obtained by an $MS^n$ (where n is an integer equal to or greater than 2) mass spectrometer, and more particularly, it relates to mass analysis data analyzing method and apparatus for estimating the structure of, for example, an unidentified substance produced through partial structural change caused by some reason from an original substance having a known structure.

BACKGROUND ART

In recent years, mass spectrometers capable of performing $MS^n$ analysis are widely used for structure analysis of various substances including polymer compounds. Specifically, when an ion originating from a component of interest contained in a sample is dissociated by collision induced dissociation (CID), a molecular bond is broken at a specific site depending on the bond energy or other factors, so that various product ions and neutral losses are produced. Therefore, an ion having a specific mass-to-charge ratio m/z corresponding to a component of interest is selected from various ions produced from a sample, the selected ion is dissociated by CID, and various product ions produced by the dissociation are subjected to mass analysis to obtain an $MS^2$ spectrum. Since the $MS^2$ spectrum includes information about various fragments (including product ions and neutral losses) originating from the component of interest, the chemical structure of the component of interest can be estimated by analyzing the $MS^2$ spectrum data.

Actually, however, it is not always easy to determine a structural formula of an unidentified substance by utilizing information collected from an $MS^2$ spectrum obtained by a single dissociation operation or from an $MS^n$ spectrum obtained through a plurality of repeated dissociation operations. A polymer compound composed of specific elements and having a one-dimensional (linear) sequence structure, such as amino acids, can be comparatively easily assessed (or estimated) for its structure from an $MS^n$ spectrum. On the contrary, general low molecular weight compounds having a molecular weight of about 50 to 1000 have a variety of structural formulas and are complicated in the sequence, and therefore, it is difficult in many cases to estimate their structures from an $MS^n$ spectrum. A structural analysis method useful in such a case is database search using a database storing $MS^n$ peak patterns and the like of known substances (see Patent Document 1, for example). Since the number of known substances stored in a database is, however, limited, the search often results in no hits.

In synthesis of, for example, a pharmaceutical, not only a substance of interest but also a large number of byproducts having similar structures are simultaneously produced, and hence, it is sometimes desired to study structural similarity and difference among various byproducts contained in a sample. Alternatively, in studying metabolism of a pharmaceutical in vivo, it may be desired to find structural similarity and difference among a large number of metabolites including an unidentified substance. In these cases, although information about a substance of interest having a known structure may be stored in a database, the database cannot generally store information about all byproducts and metabolites having slightly different structures. Therefore, there often remains an unidentified substance whose structural formula cannot be determined even if the database is searched.

BACKGROUND ART DOCUMENT

Patent Document

[Patent Document 1] US Patent Application Publication No. 2006/0085142

DISCLOSURE OF THE INVENTION

Problems to be Solved by the Invention

The present invention has been developed to solve the aforementioned problems. Its object is to provide mass analysis data analyzing method and apparatus for efficiently and highly reliably estimating, based on $MS^n$ spectrum data, the structure of an unidentified substance that is similar to or has been subjected to a structural change from an original substance having a known structure.

Means for Solving the Problems

The first aspect of the present invention aimed at solving the aforementioned problems is a mass analysis data analyzing method for estimating a structure of an unidentified substance having a partially different structure from a structurally known substance based on mass analysis data about the structurally known substance and mass analysis data about fragments obtained by one or more dissociation operations for the structurally known substance, as well as mass analysis data about the unidentified substance and mass analysis data about fragments obtained by one or more dissociation operations for the unidentified substance, the mass analysis data analyzing method including:

guessing a structural difference between the structurally known substance and the unidentified substance based on a mass difference between the structurally known substance and the unidentified substance obtained from the mass analysis data about both of the substances;

selecting a plurality of pairs each composed of a mass of a fragment originating from the structurally known substance and a mass of a fragment originating from the unidentified substance, where, in each of the pairs, a mass difference between the mass of the fragment obtained from the mass analysis data about the fragment originating from the structurally known substance and the mass of the fragment obtained from the mass analysis data about the fragment originating from the unidentified substance is equal to the mass difference corresponding to the guessed structural difference;

determining a minimum common partial structure by using information about partial structures presumed from the masses of the fragments originating from the structurally known substance paired with the fragments originating from the unidentified substance in the selected pairs on an assumption that the fragments originating from the unidentified substance included in the plurality of selected pairs correspond to partial structures different from one another; and estimating the structure of the unidentified substance based on the determined minimum common partial structure, a known structure of the structurally known substance and the guessed structural difference.

The second aspect of the present invention aimed at solving the aforementioned problems is an apparatus for carrying out the mass analysis data analyzing method according to the first aspect of the present invention. That is to say, it is a mass analysis data analyzing apparatus for estimating a structure of an unidentified substance having a partially different structure from a structurally known substance based on mass analysis data about a structurally known substance and mass analysis data about fragments obtained by one or more dissociation operations for the structurally known substance, as well as mass analysis data about the unidentified substance and mass analysis data about fragments obtained by one or more dissociation operations for the unidentified substance, the mass analysis data analyzing apparatus including:

a) a partial structure information storage unit for storing a mass of each fragment obtained from the mass analysis data about the fragments originating from the structurally known substance and a partial structure obtained from a known structure of the structurally known substance, the mass and the partial structure being associated with each other;

b) a structural difference guessing information setting unit for setting information about a structural difference between the structurally known substance and the unidentified substance, the structural difference being guessed based on a mass difference between the structurally known substance and the unidentified substance obtained from the mass analysis data about both of the substances;

c) a fragment pair selection unit for selecting a plurality of pairs each composed of a mass of a fragment originating from the structurally known substance and a mass of a fragment originating from the unidentified substance, where, in each of the pairs, the mass difference between the mass of the fragment obtained from the mass analysis data about the fragment originating from the structurally known substance and the mass of the fragment obtained from the mass analysis data about the fragment originating from the unidentified substance is equal to the mass difference derived from the guessed structural difference set by the structural difference guessing information setting unit; and d) a structural estimation unit for determining a minimum common partial structure by referring to information in the partial structure information storage unit about partial structures associated with masses of the fragments originating from the structurally known substance paired with the fragments originating from the unidentified substance in the selected pairs on an assumption that the fragments originating from the unidentified substance included in the plurality of selected pairs correspond to partial structures different from one another, and estimating the structure of the unidentified substance based on the determined minimum common partial structure, the known structure of the structurally known substance and the guessed structural difference.

In the first and second aspects of the present invention, the mass analysis data about the structurally known substance and the mass analysis data about the fragments obtained by one or more dissociation operations for the structurally known substance may be data obtained by actually subjecting the structurally known substance to mass analysis ($MS^1$ analysis) and $MS^n$ (where n is an integer equal to or greater than 2). Alternatively, it may be mass analysis data ($MS^1$ spectrum data, $MS^n$ spectrum data) previously estimated by calculation based on known information such as bond energy. On the other hand, since the unidentified substance has a structure partly unidentified, the mass analysis data about the unidentified substance and the mass analysis data about fragments obtained by one or more dissociation operations for the unidentified substance are data obtained by actually subjecting the unidentified substance to the mass analysis ($MS^1$ analysis) and $MS^n$ (where n is an integer equal to or greater than 2).

In the first and second aspects of the present invention, the "unidentified substance" to be analyzed for the structure is, for example, a substance produced from an original substance having a known structure through chemical change such as metabolism. Alternatively, it may be a byproduct produced, in synthesis or the like of an original substance, through partial replacement or loss, or addition of another component in the structure of the original substance. Also, the "unidentified substance" is not always a substance produced through change from one substance but may be any substance having a structure different from, in some part, but common to, in the other part, a structurally known substance.

In the first and second aspects of the present invention, the "fragments" refer to product ions, or both product ions and neutral losses, which are produced by dissociation. A product ion appears, as a peak, on a mass spectrum ($MS^n$ spectrum) included in mass analysis data detected by mass analysis, more specifically, created based on the mass analysis data. On the other hand, a neutral loss is not directly detected by mass analysis but obtained, for example, as a mass difference between a product ion peak and a precursor ion peak appearing on the mass spectrum ($MS^n$ spectrum).

Since the structure of the structurally known substance, such as an original substance, is known, partial structures and masses of various fragments that may be produced if various binding sites are broken in its chemical structural formula can be previously obtained by calculation. Therefore, based on mass analysis data about fragments obtained by subjecting the structurally known substance to one or more dissociation operations, actual masses of the individual fragments are obtained, so as to be compared with the masses obtained by the calculation as described above, and thus, memory information to be stored in the partial structure information storage unit can be created. Needless to say, the memory information to be stored in the partial structure information storage unit can be created by merely calculation and guess based on the calculation without performing actual measurement. Alternatively, without previously obtaining such information in which the masses of the individual fragments and the partial structures are associated with each other, as occasion demands, namely, when the mass of one fragment is given, a partial structure corresponding to the mass can be derived from the known structure of the structurally known substance.

The mass of the structurally known substance and the mass of the unidentified substance are obtained from the mass analysis data of the structurally known substance and the mass analysis data of the unidentified substance, respectively. A mass difference between these substances is attributed to a structural difference between the structurally known substance and the unidentified substance, and therefore, the structural difference can be guessed to some extent based on the mass difference. Naturally, as the structural difference is more complicated, the guess of the structural difference is more difficult. Accordingly, the present invention is applicable to structural analysis of an unidentified substance having such a comparatively small structural difference that the structural difference can be guessed based on a mass difference.

When ions of one substance are dissociated as precursor ions by the collision induced dissociation (CID) or the like, bond is broken at various sites in the one substance, resulting in producing various fragments partially having common structures but having different masses. Therefore, some of various fragments obtained by dissociating the unidentified substance should be common in a part of their structures. If the guessed structural difference is included in the common partial structure, there should exist fragments originating from the structurally known substance that have a mass different from the mass of these fragments derived from the unidentified substance, which corresponds to the mass difference derived from the guessed structural difference. Therefore, the mass of each fragment originating from the structurally known substance and the mass of each fragment originating from the unidentified substance are paired, a difference between the paired masses is calculated, so as to select a pair having a mass difference which is equal to the mass difference derived from the guessed structural difference.

If the sites of breaking the bond by the dissociation are multiple as described above, a plurality of, in general, a large number of pairs should be selected. Therefore, assuming that the fragments of the unidentified substance which are one member of the pairs correspond to partial structures having the same structural difference, information about partial structures assumed from the mass of the paired fragments originating from the structurally known substance is used for narrowing down a common partial structure in which the guessed structural difference is caused. When a minimum common partial structure is found, a partial structure which is not common can be determined based on the known structure of the structurally known substance. Therefore, based on the partial structure which is not common, the common partial structure and the guessed structural difference, the structure of the unidentified substance is estimated so as to be presented to a user by, for example, displaying a candidate for the structural formula.

However, even though the difference between the mass of the fragment originating from the structurally known substance and the mass of the fragment originating from the unidentified substance is equal to the mass difference derived from the guessed structural difference, if fragments having this mass difference are originally present in the mass analysis data about the fragments originating from the structurally known substance, the fragment originating from the unidentified substance does not always include the guessed structural difference. Therefore, in the first and second aspects of the present invention, it is preferably determined whether or not a combination of masses of a selected pairs is present in the mass analysis data about the fragments originating from the structurally known substance, and if such a selected pair is present, the selected pair is dealt with as having low reliability in estimating the structure of the unidentified substance.

Here, the simplest method for "dealing with it as having low reliability" is to exclude the pair of the masses from the structural estimation for the unidentified substance, and apart from this, for example, the dealing may be put to a user's decision. Specifically, it may be entrusted to a user to determine that the fragment originating from the unidentified substance included in the pair having the mass difference corresponding to the guessed structural difference include the structural difference or that it does not include the structural difference but is originally included in the structurally known substance. Besides, mass analysis data about fragments obtained by subjecting each of the structurally known substance and the unidentified substance to two or more dissociation operations may be used for estimating whether the fragment of interest includes the structural difference or is originally included in the structurally known substance.

Furthermore, the structural change from the structurally known substance to the unidentified substance caused by metabolism or the like (differences in structure between the structurally known substance and the unidentified substance) occurs not always in one position but may sometimes occur in two or more positions. Even if the structural difference is caused in one position, the number of structural differences that can be guessed from the mass difference between the structurally known substance and the unidentified substance is not always one. Therefore, in the first and second aspects of the present invention, if the pairs each composed of a mass of a fragment originating from the structurally known substance and a mass of a fragment originating from the unidentified substance cannot be selected, where, in each of the selected pairs, a mass difference between the mass of the fragment obtained from the mass analysis data about the fragment originating from the structurally known substance and the mass of the fragment obtained from the mass analysis data about the fragment originating from the unidentified substance is equal to the mass difference derived from the guessed structural difference, guess of the structural difference between the structurally known substance and the unidentified substance is preferably changed to estimate the structure of the unidentified substance again.

Besides, the structure is partially different between the structurally known substance and the unidentified substance not always in one position but in two or more positions in some cases as described above. Therefore, in the first and second aspects of the present invention, preferably on the assumption that the structural difference between the structurally known substance and the unidentified substance occurs in one position, the structural difference is guessed based on the mass difference between the structurally known substance and the unidentified substance obtained from the mass analysis data of these substances, and if the pairs each composed of a mass of a fragment originating from the structurally known substance and a mass of a fragment originating from the unidentified substance cannot be selected, where, in each of the selected pairs, a mass difference between the mass of the fragment obtained from the mass analysis data about the fragment originating from the structurally known substance and the mass of the fragment obtained from the mass analysis data about the fragment originating from the unidentified substance is equal to the mass difference derived from the guessed structural difference, it may be estimated that the structural difference between the structurally known substance and the unidentified substance is caused in a plurality of positions.

Incidentally, in the first and second aspects of the present invention, the mass analysis data obtained by mass analysis of fragments obtained by performing merely one dissociation operation on each of the structurally known substance and the unidentified substance used as precursor ions, namely, $MS^2$ spectrum data, can be basically used. If the structure of the unidentified substance cannot be estimated based on the $MS^2$ spectrum data alone or cannot be estimated with a sufficiently high degree of reliability, mass analysis data obtained by mass analysis of fragments obtained by performing two or more dissociation operations on each of the structurally known substance and the unidentified substance, namely, $MS^n$ spectrum data with n equal to or greater than 3, may be used.

Effects of the Invention

The mass analysis data analyzing method and apparatus according to the present invention can estimate the structure of an unidentified substance produced from a structurally known substance through partial structural change caused by chemical change such as metabolism at high efficiency and high reliability. In particular, regarding a metabolite, a byproduct or a similar compound produced from a structurally known substance of a low molecular weight compound with a molecular weight of approximately 50 to 1000 having a variety of structural formulas and having a complicated sequence, even if a database completely storing all substances partially different in structure is not provided, the structure of an unidentified substance of interest can be appropriately estimated, and information useful for a user in determining the structure of the substance can be provided.

BRIEF DESCRIPTION OF THE DRAWINGS

FIG. 6 is a diagram of an exemplified correspondence table showing mass differences between product ions obtained by $MS^2$ analysis of the original substance and product ions obtained by $MS^2$ analysis of the metabolite.

MODE FOR CARRYING OUT THE INVENTION

Figure 1:
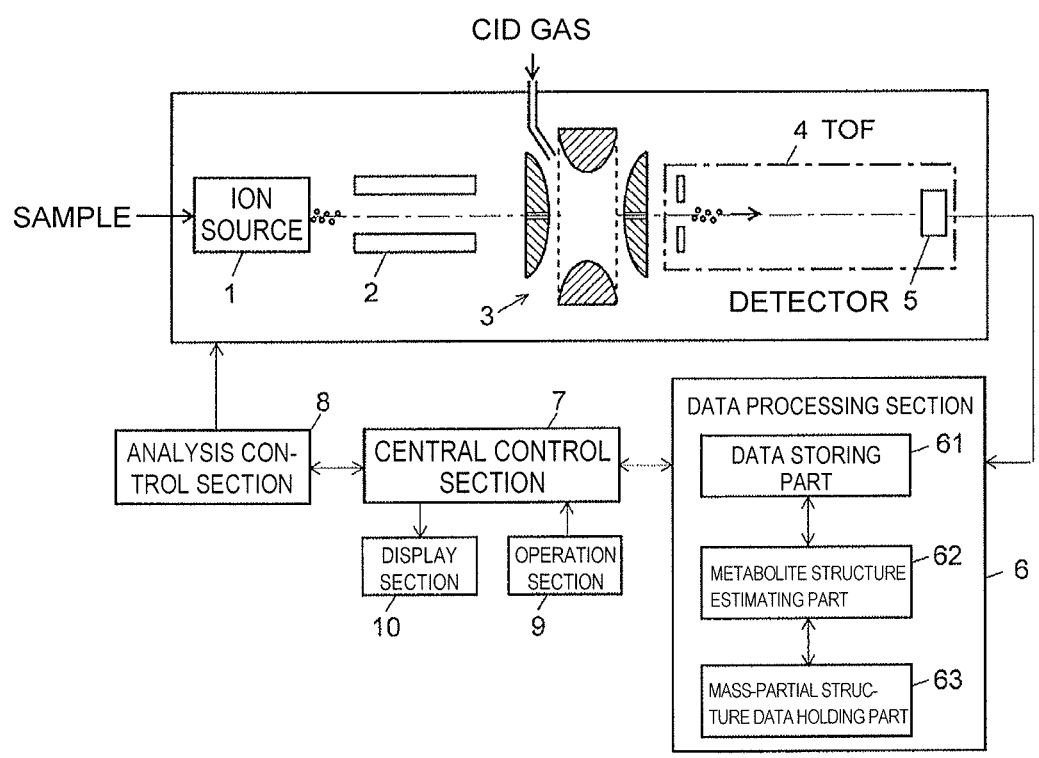
FIG. 1 is a schematic configuration diagram of a mass analysis system including a mass analysis data analyzing apparatus according to an embodiment of the present invention.

One embodiment of the mass analysis system including the mass analysis data analyzing apparatus of the present invention will now be described with reference to the accompanying drawings. FIG. 1 is a schematic configuration diagram of the mass analysis system according to the present embodiment.

A sample to be analyzed is introduced into an ion source 1, and a component contained in the sample is ionized in the ion source 1. The thus generated ions are introduced via an ion guide 2 into a three-dimensional quadrupole ion trap 3 constructed by a ring electrode and a pair of end cap electrodes, and in this ion trap, precursor ions are selected and dissociation of the precursor ions is accelerated by CID caused through a contact with an externally introduced CID gas. Various product ions produced by the dissociation are given predetermined kinetic energy to be ejected from the ion trap 3 all at once, so as to be introduced into a time-of-flight mass spectrometer (TOFMS) 4. The product ions are separated while flying in a flight space of the spectrometer, and reach an ion detector 5 with time lag to be detected. A detection signal obtained by the ion detector 5 is input to a data processing section 6. In this data processing section, flight time is converted into a mass-to-charge ratio to create an $MS^n$ spectrum, and various processes based on the spectrum data are executed.

The operations of the individual components such as the ion source 1, the ion trap 3 and the time-of-flight mass spectrometer 4 are controlled by an analysis control section 8, and the analysis control section 8 and the data processing section 6 are operated under control of a central control section 7. To the central control section 7, an operation section 9 including, for example, a keyboard or the like, and a display section 10 such as a monitor are connected. In general, many of functions of the central control section 7, the analysis control section 8 and the data processing section 6 are realized by executing a dedicated processing/controlling program installed in a personal computer. The data processing section 6 includes not only a data storing part 61 but also a metabolite structure estimating part 62 and a mass-partial structure data holding part 63, and executes characteristic data processing for estimating the structure of an unidentified metabolite.

Although the mass analysis system of FIG. 1 has a configuration in which the three-dimensional quadrupole ion trap and the time-of-flight mass spectrometer are combined, the configuration of the spectrometer is not limited to this. If, for example, the $MS^2$ analysis alone is to be executed, a triple quadrupole mass spectrometer may be used.

The mass analysis system of the present embodiment is characterized by a data analysis process for estimating the structure of one substance having an unidentified structure, such as a metabolite, a byproduct or a decomposition product, produced from an original substance having a known structural formula (a structurally known substance) through partial structural change, such as metabolism, caused by some reason. Herein, although a metabolite produced from an original substance through metabolism will be described as an example, the structural change is not limited to the metabolism, but the mass analysis system is applicable to various types of change caused by replacement, loss and addition (modification) of a partial structure. In addition, the mass analysis system is usable for estimating the structure of not only a substance produced through the structural change from an original substance but also a general unidentified substance having a partially different structure from a substance whose structure is known.

Figure 2:
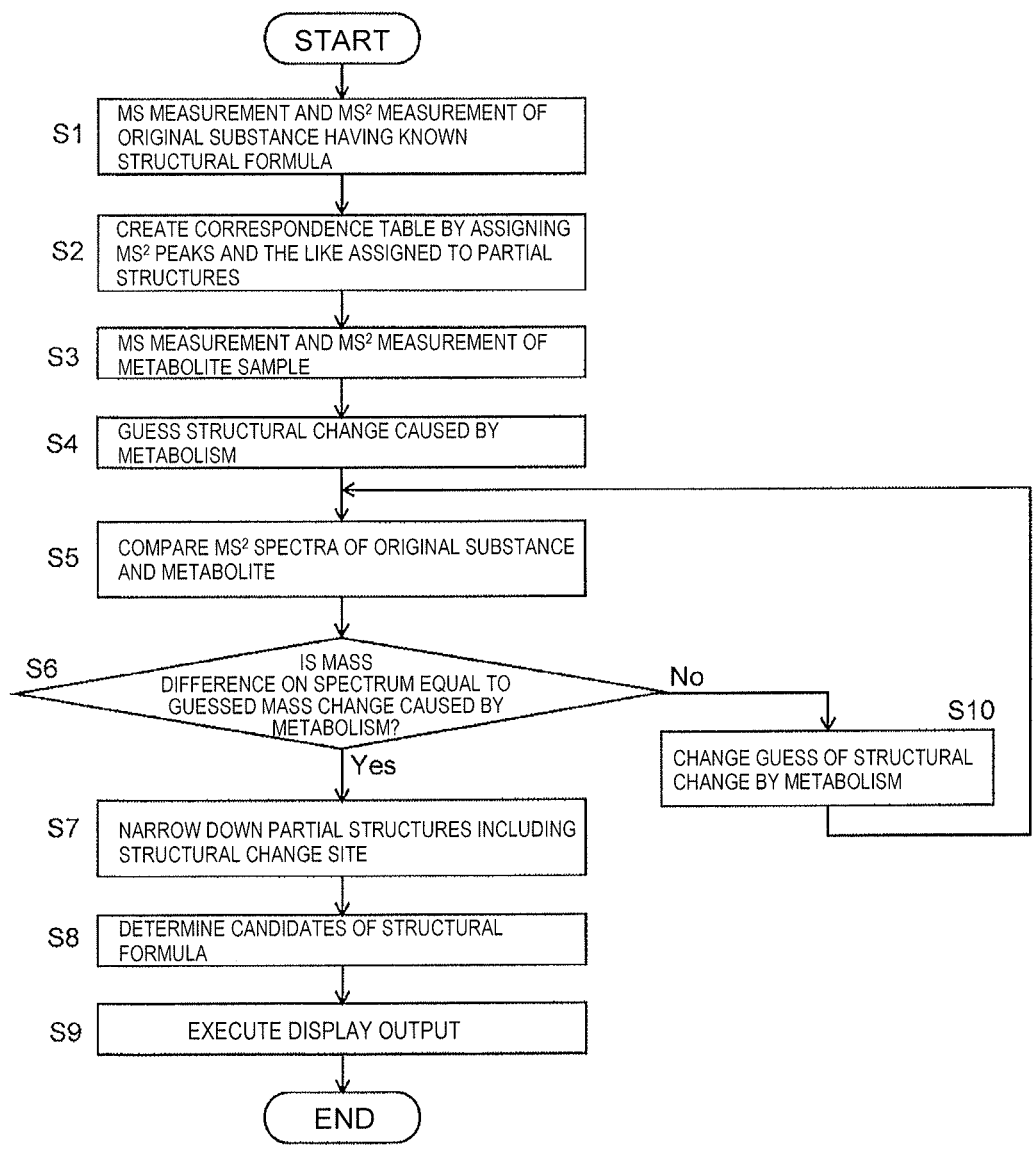
FIG. 2 is a flowchart of an exemplified procedure of a metabolite structural estimating process performed in the mass analysis system of the embodiment.
Figure 3:
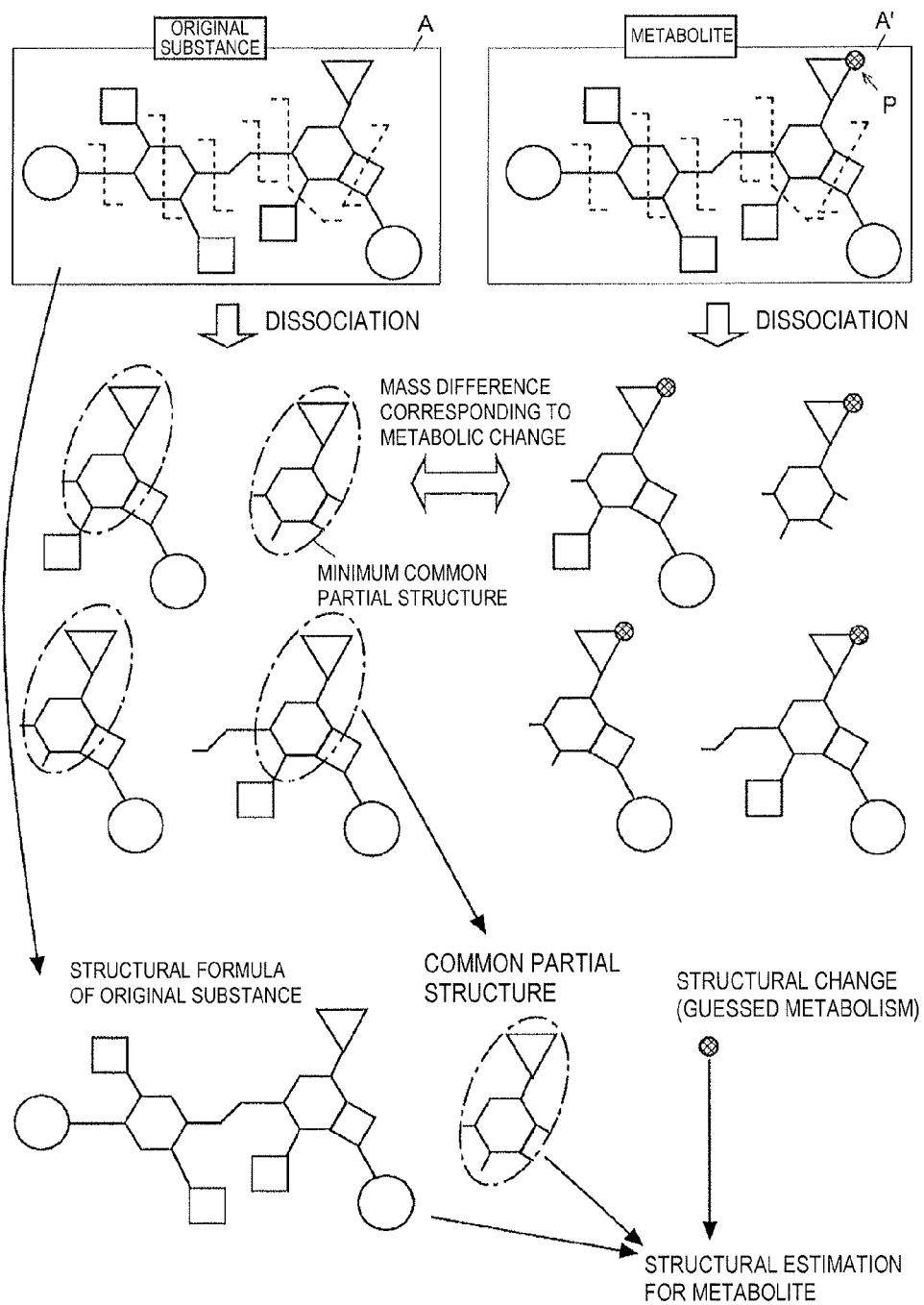
FIG. 3 is a conceptual diagram of the metabolite structural estimating process performed in the mass analysis system of the embodiment.

FIG. 2 is a flowchart illustrating an exemplified procedure of a metabolite structural estimating process including measurement of a sample. FIG. 3 is a conceptual diagram of the metabolite structural estimating process. First, the concept of the metabolite structural estimating process is described with reference to FIG. 3.

Here, an original substance A having a simplified structural formula as illustrated in FIG. 3 and a metabolite A' produced through partial structural change from the original substance A are assumed. A site indicated by P corresponds to a structural change site. The structural formula of the original substance A is known, and the structural formula of the metabolite A' is unidentified. When the original substance A is dissociated by CID or the like, bond is broken at various sites in its structure to produce various fragments. The fragments include a product ion that has a charge (namely, that can be detected by mass analysis) and a neutral loss that has a neutral property (namely, that cannot be directly detected by mass analysis), but they are not distinguished from each other (or are all assumed to be product ions) herein for simplifying the description.

The structure of the metabolite A' is mostly common to that of the original substance A, and therefore, when the metabolite A' is dissociated under the same conditions as in the dissociation of the original substance A, bond is broken at substantially the same sites as in the original substance A to produce various fragments. Among the various fragments originating from the original substance A and the various fragments originating from the metabolite A', some have the same mass (the same mass-to-charge ratio if the fragments are ions). However, if a fragment originating from the metabolite A' including the structural change site P is compared with a fragment originating from the original substance A in a state prior to the structural change, there should be a difference in the mass which corresponds to the structural change. In other words, if a mass difference between one fragment originating from the original substance A and one fragment originating from the metabolite A' is found to is equal to a mass difference corresponding to the structural change, namely, a mass difference $\Delta M$ between the original substance A and the metabolite A', it is highly probable that these fragments are the same partial structures different from each other in the structural change site P alone. Since a molecular bond is broken at various sites as described above, there should exist, as described above, a large number of pairs of fragments originating from the original substance A and fragments originating from the metabolite A' that can be regarded as a pair of the same partial structures different in the structural change site P alone.

Since the structural formula of the original substance A is known, the partial structures produced as a result of breakage of the bond at various sites can be easily obtained. When the masses of the partial structures thus obtained are compared with the masses of the respective fragments obtained by the $MS^2$ analysis, the partial structures of the individual fragments originating from the original substance A can be studied. When information thus obtained is used, in the individual pairs of the fragments originating from the original substance A and the fragments originating from the metabolite A' that can be regarded as a pair of the same partial structures different in the structural change site P alone, partial structures corresponding to the fragments originating from the original substance A can be determined. When these different partial structures are compared with one another and a minimum common partial structure can be found in them, the common partial structure is regarded as a partial structure to be changed to the structural change site P. In the metabolite A, a part other than the common partial structure should be identical to the original substance A, and in the common partial structure, the structural change corresponding to the mass difference $\Delta M$ between the original substance A and the metabolite A' is caused. Therefore, when a state of the structural change can be guessed based on the mass difference $\Delta M$, the structure of the metabolite A' can be estimated with high accuracy based on information thus obtained.

However, in order to enable the aforementioned structural estimation, there are some prerequisites. For example, if there are, among various fragments originating from the original substance A, two fragments whose mass difference is equal to the mass difference $\Delta M$ between the original substance A and the metabolite A', even though the mass difference between the fragment originating from the metabolite A' and the fragment originating from the original substance A is equal to the mass difference $\Delta M$, it cannot be determined whether the fragment originating from the metabolite A' is produced through the structural change such as metabolism or is originally identical to the fragment of the original substance A regardless of the structural change. Specifically, there is uncertainty in the discrimination in this case. Therefore, it may be previously examined whether or not there are, among various fragments originating from the original substance A, two fragments having the same mass difference as the mass difference $\Delta M$ between the original substance A and the metabolite A', so as to recognize that the fragments have at least such uncertainty and to execute processing for the uncertainty. Specifically, as possible processing, for example, information about a fragment anticipated to have such uncertainty may be excluded from the structural estimation for the metabolite, or it may be inquired of a user whether or not such a fragment is used for the structural estimation to perform processing in accordance with an instruction from the user.

Besides, it is supposed that the structural change caused by the metabolism occurs merely in one position in the above description, and if the structural change occurs at a plurality of different sites, the aforementioned simple determination cannot be made. In such a case, it is necessary to consider, for example, a combination of a plurality of structural changes.

Furthermore, although not considered in the above description, fragments include a product ion and a neutral loss, and there are cases where the structural change site P is present in a product ion and where it is present in a neutral loss. If a product ion is produced from one precursor ion, there always exists a neutral loss corresponding to the product ion. Accordingly, if the structural change site P is present in one product ion, the structural change site P is not present in a corresponding neutral loss, and therefore, there appear a large number of pairs of neutral losses in which a mass difference between a neutral loss originating from the original substance A and a neutral loss originating from the metabolite A' is 0. On the contrary, if the structural change site P is present in one neutral loss, the structural change site P is not present in a corresponding product ion, and therefore, there appear a large number of pairs of product ions in which a mass difference between a product ion originating from the original substance A and a product ion originating from the metabolite A' is 0. Accordingly, when both the mass differences between the product ions originating from the original substance A and the product ions originating from the metabolite A' and the mass differences between the neutral losses originating from the original substance A and the neutral losses originating from the metabolite A' are examined to confirm the matching between these mass differences, the reliability of the structural estimation for the metabolite A' can be improved. The procedure described later employs this method.

Furthermore, although merely the fragments produced by performing one dissociation operation on the precursor ion are assumed in the above description, fragments produced by two or more dissociation operations, namely, $MS^3$ spectrum data with n equal to or greater than 3, may be used for the structural estimation. For example, in the case where a mass difference between a fragment originating from the metabolite A' and a fragment originating from the original substance A is equal to the mass difference ΔM between the metabolite A' and the original substance A but it is uncertain whether or not the fragment originating from the metabolite A' is produced through the structural change such as metabolism as described above, information based on the $MS^3$ spectrum may be used for determining whether or not the fragment originating from the metabolite A' is produced through the structural change such as metabolism or is originally identical to the fragment originating from the original substance A.

Incidentally, in the case where there is a possibility that the structural change site P is present in one partial structure and the $MS^n$ analysis with n equal to or greater than 3 is performed for examining the possibility, an ion that has possibility of including the structural change site P and has a mass as small as possible is set as a precursor ion. Thus, the number of unnecessary product ions can be reduced, and hence information related to the structural change site P can be easily obtained.

Next, the details of the metabolite structural estimating process performed in the mass analysis system of the present embodiment is described with reference to the flowchart of FIG. 2, and FIGS. 4 to 7 illustrating an example of the actual process.

Prior to the actual analysis process, information necessary for the structural estimation for a metabolite is prepared based on a result obtained by the mass analysis of an original substance. Specifically, when the analysis is started, MS measurement and $MS^2$ measurement of an original substance having a known structural formula are executed under control of the analysis control section 8, and measurement data thus obtained is stored in the data storing part 61 (step S1). Next, the metabolite structure estimating part 62 assigns the masses of individual peaks appearing on an $MS^2$ spectrum obtained in step S1 respectively to partial structures produced through breakage of bond of the known structure of the original substance, creates a table of correspondences between masses and the partial structures, and stores the table in the mass-partial structure data holding part 63 (step S2). Alternatively, in step S1 MS spectrum data and $MS^2$ spectrum data may be obtained through calculation based on information of bond energy and the like obtained from the known structure without actually performing the MS measurement and the $MS^2$ measurement of the original substance, and in step S2 the table of correspondences between the masses and the partial structures may be created based on the thus obtained data.

Figure 4:
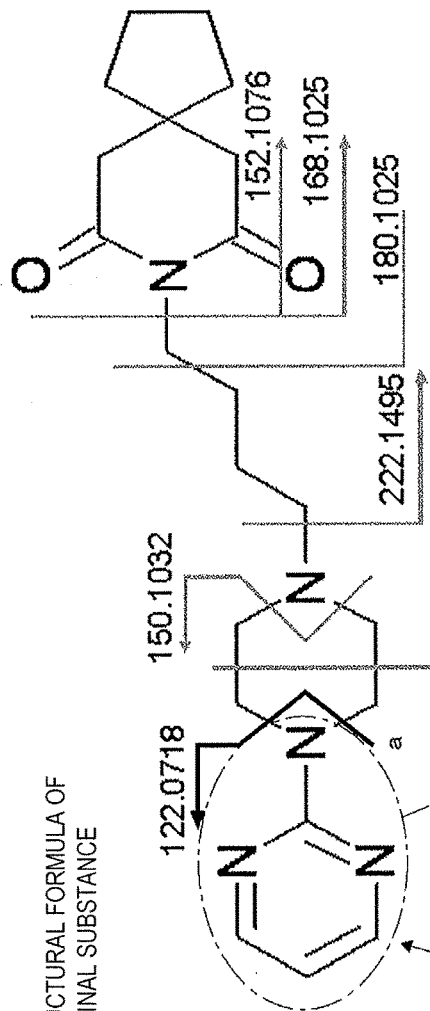
FIG. 4 is a diagram illustrating exemplified assignment of a partial structure to an $MS^2$ spectral peak of an original substance.
Figure 4:
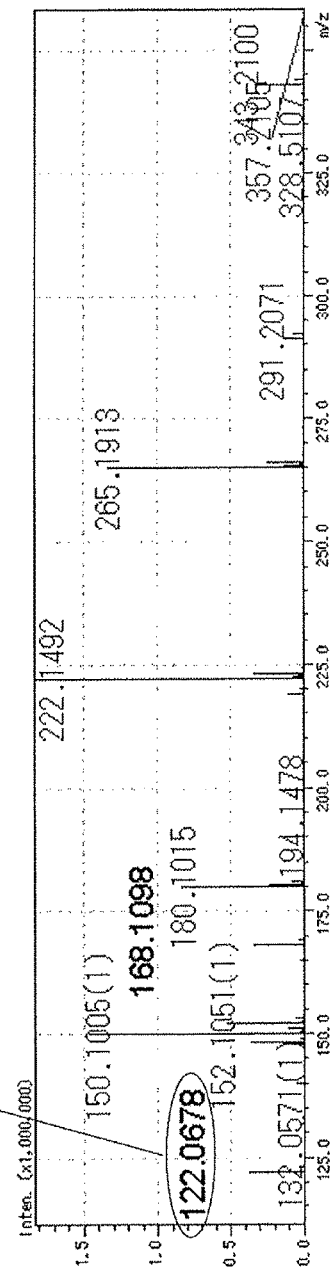

FIG. 4 is a diagram illustrating a structural formula and an $MS^2$ spectrum of buspirone herein described as an example of the original substance. By comparing mass ranges, which are determined for the masses of respective peaks appearing on the $MS^2$ spectrum based on a mass error or the like of the spectrometer, with the masses calculated from the partial structures, the individual peaks can be assigned to the respective partial structures. For example, a peak at m/z 122.0678 on the $MS^2$ spectrum is made to correspond to a product ion b produced when the bond is broken in a position a on the structural formula. In this manner, many of peaks on the $MS^2$ spectrum can be made to correspond to the partial structures. Although the peaks appearing on the $MS^2$ spectrum are attributed to product ions, fragments produced by dissociating the original substance may include neutral losses having a neutral property as described above, and a neutral loss has, on the $MS^2$ spectrum, a mass corresponding to a difference between the mass of a precursor ion and the mass of a product ion. Therefore, a table of correspondences between the masses of the neutral losses obtained from the $MS^2$ spectrum and the respective partial structures is also created to be stored in the mass-partial structure data holding part 63.

Subsequently, the MS measurement and the $MS^2$ measurement are executed on a metabolite sample having an unidentified structure (but known to have been produced from the original substance through structural change caused by metabolism), and measurement data thus obtained is stored in the data storing part 61 (step S3). Incidentally, if a plurality of metabolites are mixedly contained in the sample, ions may be automatically selected in the descending order of signal intensity based on the result of the MS measurement so as to set a selected ion as a precursor ion for executing the $MS^2$ measurement, or a mass spectrum obtained by the MS measurement may be displayed on the screen of the display section 10 so as to allow a user to select an ion peak to be analyzed, so that the selected ion can be set as a precursor ion for executing the $MS^2$ measurement.

The metabolite structure estimating part 62 guesses the type of the structural change caused by metabolism based on a mass difference between the mass obtained as a result of the MS measurement of the original substance and the mass obtained as a result of the MS measurement of the metabolite (step S4). For example, in an example described later, the original substance has an m/z value of 386.2547, the metabolite has an m/z value of 402.2500, and a mass difference between them is approximately +16. In this case, assuming that the structural change is modification caused in one position, hydroxylation (replacement of H with a hydroxyl group OH) can be one candidate of the type of the structural change. In general, as the mass difference is larger, the number of guessed types of the structural change is increased. Therefore, for example, the guessed types of the structural change are listed, and structural formula estimation processing is performed by a procedure described below for the listed types of structural change one by one. If an appropriate solution (a candidate of the structural formula of the metabolite) cannot be obtained, another candidate of the structural change included in the list may be selected for executing the structural formula estimation.

Subsequently, the metabolite structure estimating part 62 compares an $MS^2$ spectrum of the original substance and an $MS^2$ spectrum of the metabolite obtained based on the measurement data stored in the data storing part 61 (step S5). Specifically, with attention paid to differences between the masses of the individual product ions obtained from the $MS^2$ spectrum of the original substance and the masses of the individual product ions obtained from the $MS^2$ spectrum of the metabolite, and differences between the masses of the individual neutral losses obtained from the $MS^2$ spectrum of the original substance and the masses of the individual neutral losses obtained from the $MS^2$ spectrum of the metabolite, it is determined whether or not a mass difference between a pair of product ions or neutral losses, which correspond to fragments having a mass difference is equal to the mass difference between the original substance and the metabolite, is 0 (zero) (step S6).

The processing performed in step S6 can be formulated as follows. It is assumed, regarding signs used in the formula, that a precursor ion is indicated as Pre, a product ion is indicated as Pi, a neutral loss is indicated as Nls, mass change caused by metabolism is indicated as Mod, and the prime sign "'" is added if it is originating from a metabolite. Besides, since there are a large number of product ions and neutral losses produced from the original substance and the metabolite, subscripts are used for identifying these. For example, the original substance can be expressed as Pre=$Pi_n$+$Nls_n$, and the metabolite can be expressed as Pre'=Pre+Mod 0=$Pi_n$'+$Nls_n$', wherein Mod=$\Sigma$(n=1-m) $Mod_n$.

For obtaining a mass difference between a product ion originating from the original substance and a product ion originating from the metabolite, since it is not clear which product ions correspond to each other, all pairs of the product ions originating from the original substance with the product ions originating from the metabolites are basically examined in a round robin manner. The same applies to the neutral losses.

Specifically, Pi–Pi'=$\alpha$ is calculated with respect to all the pairs of the product ions, and Nls–Nls'=$\beta$ is calculated with respect to all the pairs of the neutral losses. Assuming that a partial structure corresponding to a product ion $Pi_n$' originating from the metabolite includes the structural change site P as described with reference to FIG. 3, $Pi_n$'–$Pi_n$=Mod 0 should be established. Besides, assuming that the structural change occurs in merely one position, if a partial structure corresponding to a production $Pi_n$' originating from the metabolite includes the structural change site P caused by the metabolism, a neutral loss Nls paired with the product ion $Pi_n$' does not include the structural change site P caused by the metabolism. Specifically, $Nls_n$–$Nls_n$'=0 is established. Accordingly, if the mass difference $\alpha$ between the product ions is equal to Mod 0 and the mass difference $\beta$ between the corresponding neutral losses is zero (0), it can be determined that the partial structure corresponding to the product ion $Pi_n$' includes the structural change site P caused by the metabolism. Similarly, if a partial structure corresponding to a neutral loss $Nls_n$' originating from the metabolite includes the structural change site P caused by the metabolism, the product ion $Pi_n$' paired with the neutral loss $Nls_n$' does not include the structural change site P caused by the metabolism. Specifically, $Pi_n$–$Pi_n$'=0 is established. Accordingly, if the mass difference $\beta$ between the neutral losses is equal to Mod 0 and the mass difference $\alpha$ between the corresponding product ions is zero (0), it can be determined that the partial structure corresponding to the neutral loss $Nls_n$' includes the structural change site P caused by the metabolism.

On the other hand, if there is no pair of product ions or neutral losses having the mass difference $\alpha$ of 0 or $\beta$ of 0, it can be determined that the guess of the structural change caused by the metabolism is not appropriate, or that the assumption itself of the structural change caused in one position is not appropriate. This is a case where it is determined as No in step S6, and in such a case, the guess of the structural change caused by the metabolism is changed (step S10), and the processing returns to step S5 to execute the aforementioned processing again.

If the assumption of the structural change caused in one position and the guess of the structural change caused by the metabolism are appropriate, a plurality of pairs of product ions Pi and Pi' are detected to have a mass difference with the same value as Mod 0. This is because there are a plurality of partial structures including the structural change site P as described above. Therefore, when it is determined as Yes in step S6, the metabolite structure estimating part 62 searches for a plurality of pairs of product ions Pi and Pi' detected to have a mass difference with the same value as Mod 0 as described above, and selects a minimum common partial structure by referring to the correspondence table stored in the mass-partial structure data holding part 63 (step S7).

When the minimum common partial structure is selected as described above, this partial structure is compared with the known structural formula of the original substance. Thus, the structure of a part excluding the structural change site P is found, and hence, the structural formula of the metabolite is estimated based on the structural formula of the original substance, the minimum common partial structure and the information of the guessed structural change (step S8). Incidentally, although it is thus found that the structural change site P is present in the minimum common partial structure, if there are a plurality of positions in the minimum common partial structure where the structural change site P can be present, it is unclear which position the structural change site P is present in. In this case, a plurality of candidates of the structural formula to be estimated may be obtained. Then, the thus obtained candidates of the structural formula are displayed on the screen of the display section 10 to be presented to a user (step S9).

Figure 5:
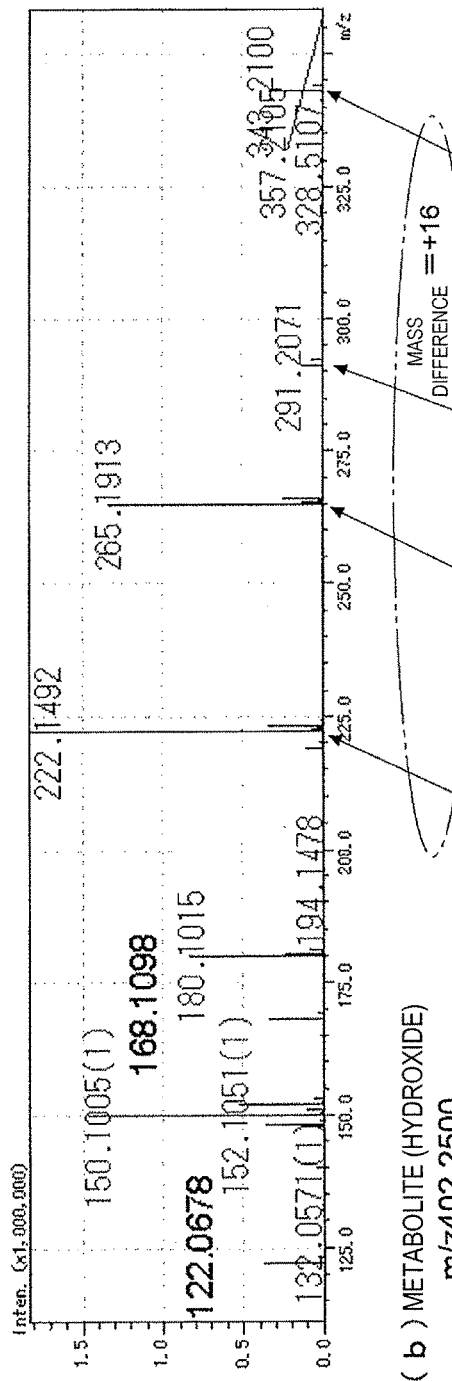
FIG. 5 is a diagram illustrating exemplified comparison between an $MS^2$ spectrum of the original substance and an $MS^2$ spectrum of a metabolite.
Figure 5:
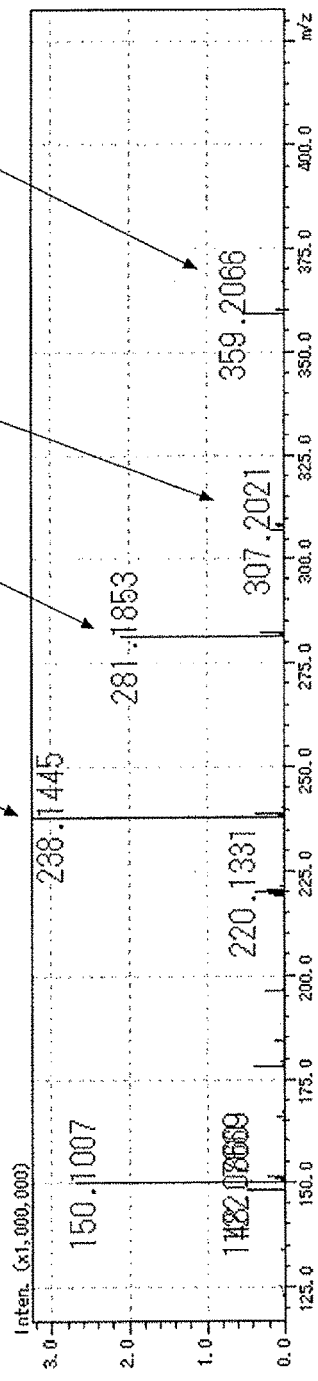

FIG. 5 illustrates the $MS^2$ spectrum of the original substance of FIG. 4 and the $MS^2$ spectrum of the metabolite having an m/z value of 402.2500. When masses (mass-to-charge ratios m/z) of peaks appearing on these $MS^2$ spectra are compared with each other, it is understood that there are a plurality of pairs of peaks shifted in mass substantially correspondingly to the mass difference between the precursor ions of the original substance and the metabolite. On the other hand, it is also understood that there are peaks having the same masses on these $MS^2$ spectra. These peaks can be said to have a possibility of the aforementioned discrimination uncertainty.

In obtaining the mass differences between the product ions originating from the original substance and the product ions originating from the metabolite in a round robin manner as described above, such processing can be easily performed by creating a table, as illustrated in FIG. 6, in which the masses of these product ions are aligned respectively in a row direction and in a column direction and the calculated mass differences are put in the intersecting cells. FIG. 6 is a table in which masses and mass differences obtained from the peaks appearing on the $MS^2$ spectra of the original substance and the metabolite of FIG. 5 are listed. It is easily understood that some pairs of product ions listed in this table have a mass difference of +16 corresponding to the mass difference between the original material and the metabolite.

Figure 7:
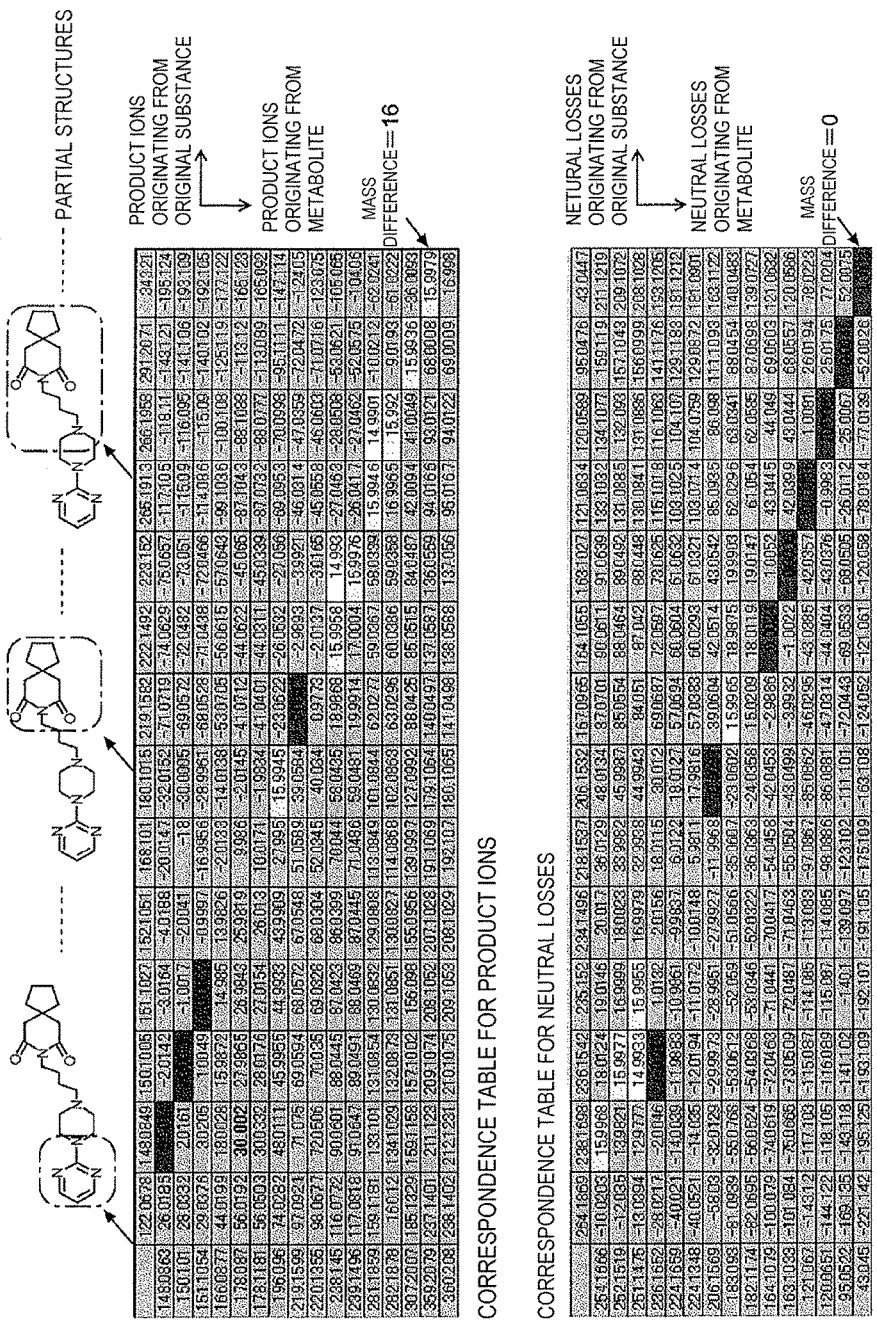
FIG. 7 is a diagram of an exemplified correspondence table showing mass differences between product ions obtained by the $MS^2$ analysis of the original substance and product ions obtained by the $MS^2$ analysis of the metabolite, and an exemplified correspondence table showing mass differences between neutral losses obtained by the $MS^2$ analysis of the original substance and neutral losses obtained by the $MS^2$ analysis of the metabolite.

FIG. 7 illustrates a table of the mass differences obtained in the same pairs of product ions as those of FIG. 6 in an upper portion and a table of mass differences obtained in pairs of corresponding neutral losses in a lower portion. Positions of cells in the upper and lower tables correspond to each other, and it is understood that the mass difference is 0 (zero) in many of cells of the lower table corresponding to cells having the mass difference of +16 in the upper table. The pairs of product ions and the pairs of neutral losses corresponding to these cells meet the aforementioned conditions that the mass difference $\alpha$ of the product ions is equal to Mod 0 and the mass difference $\beta$ of the corresponding neutral losses is 0 (zero), and therefore, it can be determined that the partial structure corresponding to the product ion $Pi_n$' includes the structural change site P caused by the metabolism. In a portion above the upper table of FIG. 7, some of partial structures (each surrounded with an alternate long and short dash line) based on the correspondence table stored in the mass-partial structure data holding part 63 are illustrated as examples. In this manner, each mass of the product ions originating from the original substance corresponds to a partial structure, and therefore, the minimum common partial structure can be easily found in the partial structures of the product ion $Pi_n'$ determined to include the structural change site P caused by the metabolism.

However, in the case where peaks having the same mass difference as Mod 0 are originally present on the $MS^2$ spectrum of the original substance, the peaks appear also on the $MS^2$ spectrum of the metabolite, and hence, it is apprehended that the peak is determined as a partial structure including the structural change site P, namely, as a partial structure having been metabolized, although it does not actually include the structural change site P. Therefore, before performing the comparison of step S5, it is determined whether or not peaks having the same mass difference as Mod 0 are originally present on the $MS^2$ spectrum of the original substance. It can be easily determined by, for example, creating a table in which the masses of the product ions originating from the original substance are aligned in a row direction and a column direction with calculated mass differences between them put in corresponding cells. If, in this table, a difference between the mass M1 of one product ion and the mass M2 of another product ion is substantially equal to Mod 0, this is probably because product ions having the same mass difference as the structural change site P are unexpectedly produced in dissociating the structure of the original precursor ion. In this case, there is a possibility that a peak having the same mass as the mass M2 on the $MS^2$ spectrum of the metabolite may be either a partial structure having the mass M1 and having been partly changed at the structural change site P by the metabolism or a partial structure the same as that having the mass M2. This is the aforementioned discrimination uncertainty. Accordingly, based on the result of the above-described prior determination, the structural estimation for the metabolite may be performed by, for example, excluding the product ions (or neutral losses) having the uncertainty from the structural estimation.

In the specific example described in the aforementioned embodiment, it is assumed that the structural change caused by the metabolism occurs in a partial structure corresponding to a product ion. It is obvious that the same method can be employed for the structural estimation for a metabolite even if the structural change caused by the metabolism occurs in a partial structure corresponding to a neutral loss. In such a case, needless to say, in the upper and lower tables of FIG. 7, a mass difference between neutral losses corresponding to the structural change caused by the metabolism is to be found in the lower table, and a pair of product ions having a mass difference of 0 (zero) is to be found in the upper table. Also in this case, as described above, it is necessary to perform the prior determination processing to determine whether or not there are ions accidentally having the same mass difference regardless of the structural change.

It is noted that the present embodiment is described as an example of the present invention, and it is evident that any modification, change or addition appropriately made within the spirit of the present invention will fall within the scope of appended claims.

EXPLANATION OF NUMERALS

1 . . . Ion source
2 . . . Ion guide
3 . . . Ion trap
4 . . . Time-of-flight mass spectrometer
5 . . . Ion detector
6 . . . Data processing section
61 . . . Data storing part
62 . . . Metabolite structure estimating part
63 . . . Mass-partial structure data holding part
7 . . . Central control section
8 . . . Analysis control section
9 . . . Operation section
10 . . . Display section

The invention claimed is:

1. A mass analysis method for estimating a structure of an unidentified substance having a partially different structure from a structurally known substance based on mass analysis data about the structurally known substance and mass analysis data about fragments obtained by one or more dissociation operations for the structurally known substance, the mass analysis data analyzing method comprising:
 performing one or more dissociation operations for the unidentified substance by using a mass analyzer to obtain mass analysis data about the unidentified substance and mass analysis data about fragments;
 determining a candidate a structural difference between the structurally known substance and the unidentified substance based on a mass difference between the structurally known substance and the unidentified substance obtained from the mass analysis data about both of the substances;
 selecting a plurality of pairs each composed of a mass of a fragment originating from the structurally known substance and a mass of a fragment originating from the unidentified substance, where, in each of the pairs, a mass difference between the mass of the fragment obtained from the mass analysis data about the fragment originating from the structurally known substance and the mass of the fragment obtained from the mass analysis data about the fragment originating from the unidentified substance is equal to the mass difference corresponding to the candidate structural difference;
 determining a minimum common partial structure by using information about partial structures presumed from the masses of the fragments originating from the structurally known substance paired with the fragments originating from the unidentified substance in the selected pairs on an assumption that the fragments originating from the unidentified substance included in the plurality of selected pairs correspond to partial structures different from one another; and
 estimating a candidate of the structure of the unidentified substance based on the determined minimum common partial structure, a known structure of the structurally known substance and the candidate structural difference,
 outputting the candidate of the structure of the unidentified substance, whereby identifying the unidentified substance on which the one or more dissociation operations are performed by the mass analyzer is improved by determining the minimum common partial structure.

2. The mass analysis method according to claim 1, wherein the fragments are product ions, or both product ions and neutral losses.

3. The mass analysis method according to claim 2, wherein it is determined whether or not a combination of masses of a selected pair is present in the mass analysis data about the fragments originating from the structurally known substance, and when a selected pair is present, the selected pair is taken as having low reliability in estimating the structure of the unidentified substance.

4. The mass analysis method according to claim 2, wherein when the pairs each composed of a mass of a fragment originating from the structurally known substance and a mass of a fragment originating from the unidentified substance is unable to be selected, where, in each of the selected pairs, a mass difference between the mass of the fragment obtained from the mass analysis data about the fragment originating from the structurally known substance and the mass of the fragment obtained from the mass analysis data about the fragment originating from the unidentified substance is equal to the mass difference derived from the candidate structural difference, the candidate structural difference between the structurally known substance and the unidentified substance is changed to estimate the structure of the unidentified substance again.

5. The mass analysis method according to claim 2,
wherein on the assumption that the structural difference between the structurally known substance and the unidentified substance is caused in one position, the candidate structural difference is determined based on the mass difference between the structurally known substance and the unidentified substance obtained from the mass analysis data of the structurally known substance and the unidentified substance, and when the pairs each composed of a mass of a fragment originating from the structurally known substance and a mass of a fragment originating from the unidentified substance is unable to be selected, where, in each of the selected pairs, a mass difference between the mass of the fragment obtained from the mass analysis data about the fragment originating from the structurally known substance and the mass of the fragment obtained from the mass analysis data about the fragment originating from the unidentified substance is equal to the mass difference derived from the candidate structural difference, it is estimated that the structural difference between the structurally known substance and the unidentified substance is caused in a plurality of positions.

6. A mass analysis apparatus for estimating a structure of an unidentified substance having a partially different structure from a structurally known substance, comprising:
a mass analyzer that obtains mass analysis data about the unidentified substance and mass analysis data about fragments obtained by one or more dissociation operations for the unidentified substance;
a data processing section, including
  a) a partial structure information storage unit for storing a mass of each fragment obtained from mass analysis data about the fragments originating from the structurally known substance obtained by one or more dissociation operations for the structurally known substance and a partial structure obtained from a known structure of the structurally known substance, the mass and the partial structure being associated with each other;
  b) a structural difference candidate information setting unit for setting information about a candidate structural difference between the structurally known substance and the unidentified substance, the candidate structural difference being determined based on a mass difference between the structurally known substance and the unidentified substance obtained from the mass analysis data about both of the substances;
  c) a fragment pair selection unit for selecting a plurality of pairs each composed of a mass of a fragment originating from the structurally known substance and a mass of a fragment originating from the unidentified substance, where, in each of the pairs, a mass difference between the mass of the fragment obtained from the mass analysis data about the fragment originating from the structurally known substance and the mass of the fragment obtained from the mass analysis data about the fragment originating from the unidentified substance is equal to the mass difference derived from the candidate structural difference set by the structural difference candidate information setting unit; and
  d) a structural estimation unit for determining a minimum common partial structure by referring to information in the partial structure information storage unit about partial structures associated with masses of the fragments originating from the structurally known substance paired with the fragments originating from the unidentified substance in the selected pairs on an assumption that the fragments originating from the unidentified substance included in the plurality of selected pairs correspond to partial structures different from one another, and estimating a candidate for the structure of the unidentified substance based on the determined minimum common partial structure, the known structure of the structurally known substance and the candidate structural difference; and
an output device that outputs the candidate of the structure of the unidentified substance, whereby identifying the unidentified substance on which the one or more dissociation operations are performed by the mass analyzer is improved by determining the minimum common partial structure.

* * * * *